United States Patent [19]

Ball et al.

[11] 4,368,263

[45] Jan. 11, 1983

[54] PRODUCTION OF CEPHALOSPORINS

[75] Inventors: Christopher Ball, Barrow-in-Furness; John S. Collins, Ulverston; Paul F. Hamlyn, Nottingham, all of England

[73] Assignee: Glaxo Group Limited, London, England

[21] Appl. No.: 33,187

[22] Filed: Apr. 25, 1979

[30] Foreign Application Priority Data

Apr. 26, 1978 [GB] United Kingdom ............... 16528/78

[51] Int. Cl.³ .............................................. C12P 35/00
[52] U.S. Cl. ....................................... 435/47; 435/48;
435/49; 435/172; 435/254; 435/911
[58] Field of Search ..................... 435/172, 47, 48, 49, 435/254

[56] References Cited

U.S. PATENT DOCUMENTS 3,929,577  12/1975  Kanzaki et al. ..................... 435/172

OTHER PUBLICATIONS

Anne' et al., Journal of General Microbiology 92, 413-417 (1976).
Nuesch et al., Genetics of Industrial Microorganisms vol. II, pp. 317-321 (1973).
Esser, Endeavour vol. 1, No. 3/4.148 pp. 143-148 (1977).

Primary Examiner—Alvin E. Tanenholtz
Attorney, Agent, or Firm—Bacon & Thomas

[57]  ABSTRACT

An improved strain of *Acremonium chrysogenum* may be produced by submitting parent strains of *Acremonium chrysogenum* to protoplast fusion and nuclear fusion and selecting said improved strain from the progeny or from a mutant thereof.

The improved strains have operational advantages for the production of cephalosporins compared with the parental strains.

The invention also relates to a method of producing a cephalosporin by culturing the improved strain of *Acremonium chrysogenum*.

12 Claims, No Drawings

PRODUCTION OF CEPHALOSPORINS

This invention concerns improvements in the production of cephalosporins. More particularly the invention is concerned with the production of improved strains of the fungal species *Acremonium chrysogenum* (formerly known as *Cephalosporium acremonium*) useful for the production of cephalosporins.

Cephalosporin C is produced commercially by culturing *A. chrysogenum* and extracting cephalosporin C from the culture medium. Although other fungal species also produce cephalosporin C, they are not of commercial interest for this purpose. Furthermore, it is known that other cephalosporins, such as desacetyl- and desacetoxy-cephalosporin C, may also be produced by culturing *A. chrysogenum*.

Considerable efforts have already been made to select strains of *A. chrysogenum* which show optimum properties for cephalosporin production. The primary property which is sought is, of course, the production of a high yield of the desired cephalosporin. However there are other features which are desirable in a strain used for commercial production, such as good sporulation and high growth rate in surface agar or submerged culture. The selection of desirable strains from natural or induced mutants is a slow process. A major reason for the slow progress of such work is the likelihood that in selecting for one desirable property (such as the production of a high yield of cephalosporin) another desirable property (such as high growth rate) will be impaired. Thus it would be highly desirable to be able to cross different strains of *A. chrysogenum* to produce an improved strain containing the best features of two parent strains.

The crossing of different strains of *A. chrysogenum* is a matter of considerable difficulty. This species has mainly uninucleate hyphal compartments and lacks a sexual cycle. It has been claimed (Nuesch et al., Gen. Ind. Microorg. (1973) II pages 317–321) that occasionally heterokaryons can be synthesised in *A. chrysogenum* by mixed cultures of germinating conidia and can give rise to derivatives of nuclear fusion either directly or preferably after prior selection of heterozygotes. This method, in our experience, is very laborious, inefficient and unreliable, especially when an attempt is made to cross divergent strains. Although this method is of some theoretical interest, it is hardly a practicable way of producing improved strains of *A. chrysogenum* for the commercial production of cephalosporins.

We have now found that different strains of *A. chrysogenum*, even strains of a highly divergent nature, can be efficiently crossed using protoplast fusion to produce recombinant segregants or other products of nuclear fusion.

One aspect of our invention is a method of producing an improved strain of *A. chrysogenum* which comprises submitting parent strains of *A. chrysogenum* to protoplast fusion and nuclear fusion and selecting said improved strain from the progeny or from a mutant thereof.

By "an improved strain" we mean a strain having operational advantages for the production of cephalosporins compared with the parental strains. Examples of such operational advantages include improved sporulation, growth rate or titre of cephalosporin; improved stability; improved growth characteristics on different media; improved ease of extraction, etc.

Another aspect of the invention is a method of producing a cephalosporin which comprises culturing an improved strain of *A. chrysogenum*, produced by protoplast fusion and nuclear fusion of parent strains of *A. chrysogenum* and selecting said improved strain from the progeny or a mutant thereof, and isolating the desired cephalosporin or a derivative thereof from the culture medium.

In producing the improved strain, the parent strains of *A. chrysogenum* may be selected to exhibit collectively properties desired in the cross (i.e. in the products of nuclear fusion), such as high yield of cephalosporin, good growth rate and good sporulation. However this is not essential, and sometimes the progeny may exhibit an advantageous property not found in the parent strains.

It is desirable, though not essential, to treat the parent strains in such a way as to facilitate the selection of the progeny. For example, the parent strains may be genetically marked e.g. with auxotrophic markers. The use of auxotrophic markers simplifies the selection of the progeny, since minimal media can be used to prevent growth of parent strains. Other markers which could be used include colour and drug resistance.

It is desirable to use marked strains which do not exhibit high frequency reverse mutation of markers so that selectants from crosses can be classified with high probability as non-revertants. Furthermore, the selection procedure is simplified if there are at least two auxotrophic markers in each parent strain. This reduces the growth rate of the parent strains on minimal media practically to zero, and further reduces the probability of revertants making significant growth on minimal media.

Markers can be introduced into the parent strains in conventional manner, by mutagenic chemicals or radiations, or marked strains resulting from natural mutations can be obtained by conventional procedures.

In an alternative method the parent strains are each treated with a different irreversible metabolic inhibitor prior to protoplast fusion and nuclear fusion. Thus each parent strain has different and complementary aspects of its metabolism inhibited. The treated parent strains may then be submitted to protoplast fusion and nuclear fusion after removal of any unreacted inhibitors. It will be appreciated that as a result of the induced metabolic inhibitory effects the only cells capable of growth are those which result from fusion of the parent strains, the non-inhibited aspects of metabolism of each parent strain complementing each other sufficiently to ensure cell survival. This technique is described by W. E. Wright in Experimental Cell Research 112 (1978) 395–407.

Prior to formation of protoplasts, the parent strains are cultured to a suitable population size in conventional manner, e.g. in shake flasks. The nature of the culture medium can influence the protoplast yield but will generally be conventional for the growth of *A. chrysogenum*. Also, the maximum yield of protoplasts is obtained from the mycelium of the cultured parent strains near the end of the phase of exponential growth. The mycelium is then recovered by filtration or centrifugation and washed to remove the culture medium.

We have found that the yield of protoplasts is greatly improved by treatment of the recovered mycelium with a thiol sensitiser, i.e. a thiol compound which assists protoplast production. The preferred thiol sensitiser is dithiothreitol, preferably at a concentration of from 0.005 M to 0.1 M, e.g. about 0.01 M, and a pH in the range 6–8.5, e.g. about 7.3. Using dithiothreitol (0.01 M) the mycelium may be incubated for e.g. 15 mins–3 hours at 20°–40° C., preferably for ½–1½ hours at about 30° C. and pH 7.3. Other thiol sensitisers include 2-mercaptoethanol, cysteamine and thioglycollate.

The treated mycelium is then washed and treated with a protoplastogenic combination of enzymes. A number of suitable enzyme combinations are commercially available, such as Cytophaga enzyme $L_1$ (BDH, Poole) and Oxoporus cellulase (E. Merck, Darmstadt, Germany). These preparations are undefined mixtures containing several enzymes, e.g. β-glucanase, chitinase, protease and lipase. The mycelium is incubated with the enzyme preparation until a satisfactory yield of protoplasts is obtained. The pH and temperature of the incubation medium and the time of incubation should be selected in accordance with the properties of the enzyme used, e.g. about pH 6.8 at about 30° C. for about 3 hours in the case of Cytophaga enzyme $L_1$. Typical enzyme concentrations are in the ranges 0.05–20 mg/ml, e.g. about 2 mg/ml, for Cytophaga enzyme $L_1$, and 2–40 mg/ml for Oxoporus cellulase. It is also important to ensure that the osmotic pressure of the medium is in a range to ensure stability of the protoplasts, e.g. equivalent to 0.5 M–1.0 M, preferably about 0.9 M, sodium chloride. The osmotic pressure of the incubation medium may be adjusted with inorganic salts, for example sodium chloride, or with a sugar or a sugar alcohol. It is advantageous to include magnesium e.g. as magnesium sulphate at 0.005–0.1 M, preferably about 0.02 M.

The following criteria are thought to be adequate to characterise protoplasts: osmotic fragility; loss of rigidity resulting in a spherical form; and observations of the release of the protoplasts through a pore leaving behind the empty cell walls.

After incubation, the mixture of protoplasts and partly digested mycelium is separated, e.g. by filtration through a medium of suitable pore size such as a layer of cotton wool, or by mild centrifugation e.g. at 200–300 g for about 5 minutes. If necessary the separation process may be repeated. The filtrate or supernatant is a suspension consisting largely of protoplasts, together with some mycelial fragments. The protoplasts may be washed, by centrifuging, e.g. at 700 g for 5 minutes, and resuspending in osmotic stabilising solution (e.g. 0.9 M sodium chloride) once or twice, and finally resuspended in the osmotic stabilising solution.

Instead of using mycelium, it is also possible to prepare the protoplasts from conidia or arthrospores of *A. chrysogenum* using similar techniques.

The viability of the protoplasts may be checked by plating out onto osmotically stabilised (e.g. with 2% sucrose and 0.8 M sodium chloride) and non-stabilised growth media. The protoplasts are osmotically fragile and do not survive on non-stabilised media after plating out from water-washed suspensions. Thus any growth on these media results from mycelial fragments present as a contaminant in the protoplast preparation. On the stabilised medium, a high proportion of the protoplasts are usually viable and eventually form colonies. The viability of the protoplasts varies between about 5 and 80%. Between about 5 and 20% of the growth on stabilised agar is due to mycelial fragments. Since the protoplasts are osmotically fragile, care should be taken at all stages of the process to ensure an adequate osmotic buffering of the medium.

Protoplasts from the parental strains are then mixed. In order to maximise the probability of the desired fusion between the protoplasts from two or more parent strains, it is preferable to employ approximately equal numbers of viable protoplasts from each strain. If desired, the mixture of protoplasts can be prepared from a mixture of mycelium from the parent strains, but there is generally no advantage in this procedure.

The protoplasts are fused in the presence of a fusogen. Although some fusion takes place spontaneously, the probability of such spontaneous fusion is too low to be useful. Many reagents have some fusogenic activity, but we prefer polyalkylene glycols, especially polyethylene glycol. Preferably the polyethylene glycol has a molecular weight in the range 1000–8000, e.g. about 6000. The glycol is employed as a solution in an aqueous buffer, preferably at a concentration of 20–60%, e.g. about 30%. The pH is suitably in the range 5–10, e.g. about 7.5. The process is preferably assisted by calcium ions, e.g. at a concentration of 0.002–1.0 M, e.g. about 0.01 M. Aggregation of the protoplasts takes place rapidly, and the reagent is typically allowed to act for from 1 minute to 2 hours, e.g. 5–20 minutes, at incubation temperatures of 0°–30° C., e.g. 25° C.

The fusogenic reagent is then diluted out with osmotic stabilising solution and the protoplasts (some of which have now fused) are centrifuged and washed. The washing medium should be isotonic with the protoplasts, e.g. 0.9 M sodium chloride.

The selection of the desired products of nuclear fusion can take place by substantially conventional methods. When auxotrophic parent strains have been used, the fusion mixture may be plated on to osmotically stabilised minimal regeneration media, sometimes supplemented but always so chosen that parent strains cannot grow but certain products of nuclear fusion and any heterokaryons formed are able to grow. Strains of the two latter types are prototrophic. It is found that prototrophs of two general types are recovered, namely stable and unstable. The stable prototrophs are characterised by approximately equal numbers of colonies on a complete medium and on a minimal medium at equivalent plating densities, following subculture on complete medium. These strains are recombinant segregants, and can be propagated indefinitely using conventional techniques. They may be expected to exhibit characteristics derived from both parent strains. These stable prototrophic recombinant segregants do not segregate by treatment with recombinogenic agents such as p-fluorophenylalanine or gamma rays, i.e. they show no change in genetic constitution with respect to the markers used in the recombination process.

The unstable prototrophs, after purification by culturing on minimal media, exhibit eventual instability on complete media by giving rise to auxotrophs.

Apart from the prototrophic progeny discussed above, plating of the fusion mixture onto a series of selective regeneration media can sometimes allow recovery of all the alleles used in the recombination process as described in Example 1. The selection of an improved strain from among the products of nuclear fusion obtained can proceed in the same manner as a conventional breeding programme, and will depend primarily on the particular combination of characteristics which is being sought in the progeny. In accordance with conventional practice, a large number of products of nuclear fusion should be tested to improve the probability of finding a strain which is significantly superior to the parent strains. If desired, such a strain may be submitted to a mutation programme with the object of further improving it.

We believe that cephalosporin-producing products of nuclear fusion, e.g. recombinant segregants, derived from the species *A. chrysogenum* by protoplast fusion have not previously been prepared, and such organisms form another aspect of our invention.

The improved strain may be cultured to produce the desired cephalosporin by known and conventional methods.

Thus the strain may be cultured under aerobic conditions, preferably in submerged culture, with shaking or stirring with air or oxygen. The fermentation medium employed should contain an assimilable source of carbon, a digestible source of nitrogen and, if desired, growth-promoting substances as well as inorganic salts.

Suitable carbon sources include, for example, glucose, sucrose, starch, soluble starch, n-paraffins, vegetable and animal oils, acetic acid, methanol, glycerol, sorbitol and ethanol.

Suitable nitrogen sources include, for example, natural nitrogen-containing substances or materials produced from them, such as meat extracts, peptone, casein, cornsteep liquor, yeast extracts, soya bean flour, tryptone, cotton seed meal and wheat bran. Nitrogen-containing organic or inorganic compounds may also be used, for example, urea, nitrates and ammonium salts such as ammonium acetate, ammonium chloride, ammonium sulphate and ammonium phosphate.

Inorganic salts which may be used in the fermentation medium may be, for example, sulphates, nitrates, chlorides, carbonates and phosphates of potassium, magnesium and calcium.

Growth-promoting substances which may be used include, for example, cysteine, cystine, thiosulphate, methyl oleate and, in particular, methionine and also trace elements such as iron, zinc, copper and manganese.

Culturing conditions such as temperature, pH and fermentation time, are selected such that the strain employed may accumulate a maximum amount of the desired cephalosporin. For example, the fermentation is advantageously carried out at a temperature ranging from 15°–45° C., preferably about 25° C., at a pH of from 4–9 preferably about 6, and for from 1–20 days, preferably 4–10 days.

The separation of the desired cephalosporin from the culture broth is conveniently carried out by conventional means, for example by filtering the culture broth, if appropriate in the presence of a filter aid such as a diatomaceous earth, washing the cells with water and then recovering the desired cephalosporin from the mixture of the filtrate and washings.

The culture broth or filtrate may optionally be initially treated with an acid such as a mineral acid to precipitate sparingly soluble salts and some proteinaceous material from the nutrient solution or to destroy any penicillin N which may be present. Penicillin N may also be destroyed by treatment with penicillinase. The culture broth or filtrate may optionally be further prepurified by solvent extraction or by ion-exchange adsorption in order to remove lipophilic impurities.

In order to recover the desired cephalosporin, conventional methods, for example absorption or adsorption chromatography, or precipitation methods, may be used.

Absorbants or adsorbants which may be used include active charcoal, ion-exchange resins and non-ionic adsorption resins. Elution of the cephalosporin may be achieved using, in particular, aqueous solutions. Particularly preferred ion-exchange resins are weakly basic anion exchangers from which the cephalosporin may be eluted with, for example, buffered ammonium, sodium or potassium acetate. Strongly basic anion exchange resins, from which the cephalosporin can be eluted with, for example, M acetic acid, may also be used. Non-ionic adsorption resins include styrene polymers, cross-linked with divinylbenzene, of large surface area, such as Amberlite XAD-4; the cephalosporin may be eluted with an aqueous alcohol or ketone such as aqueous isopropanol or aqueous acetone.

The cephalosporin may be precipitated from aqueous solution using, for example, water-miscible organic solvents such as ketones, for example acetone, or lower alkanols.

The cephalosporin may also be precipitated from concentrated aqueous solutions in the form of a metal salt such as an alkali metal salt, for example sodium or potassium.

It may be desirable to convert the fermented cephalosporin into a derivative thereof before isolation by, in particular, reaction of either the 7- or 3-side-chains. Thus the amino group of the 7-side-chain may be substituted by a group of the type described in, for example, British Patent Specification Nos. 1,041,985, 1,302,015 or 1,313,207, such as an aryl group (e.g. 2,4-dinitrophenyl), an acyl group, particularly a lower alkanoyl group (e.g. acetyl), a halo-lower alkanoyl group (e.g. chloroacetyl or dichloroacetyl), an aroyl group (e.g. benzoyl, chlorobenzoyl, nitrobenzoyl or tosyl), a lower alkoxycarbonyl group (e.g. t-butoxycarbonyl), an aryl lower alkoxycarbonyl group (e.g. benzyloxycarbonyl) or a di-acyl group such as phthaloyl. The 7-side-chain may also be converted into a 4-carboxybutanamido compound, for example by the method of British Patent Specification No. 1,272,769 or into a dihydropyridine derivative such as a 5-carboxy-5-(2,6-dimethyl-3,5-dicarboethoxy-1,4-dihydropyrid-1-yl)-pentanamido group by the method of British Patent Specification No. 1,355,347. Cephalosporin C may be converted into desacetylcephalosporin C by treatment with an esterase, for example by the method of British Patent Specifications Nos. 1,080,904 or 1,474,519.

The method used to isolate the derivative of the fermented cephalosporin will depend on the nature of the product and the reaction used, but will in general employ conventional techniques.

In order that the invention may be better understood the following Examples are given by way of illustration. The description of the strains of *A. chrysogenum* used in the following Examples was in agreement with that in 'Cephalosporium-artige Schimmelpilze (Hyphomycetes)' by Walter Gams, (Gastav Fischer Verlag, W. Germany)

EXAMPLE 1

Two auxotrophic mutants derived from *A. chrysogenum* strain M8650 (ATCC 14553) were crossed. The cross was Red Arg Leu (IMI227144)×Whi Arg Met (IMI227145). The abbreviations Arg, Met, Leu indicate a requirement for arginine, methionine or leucine respectively. "Red" indicates red mycelial pigmentation and "Whi" indicates white mycelial pigmentation. The Arg mutants were nonallelic.

The two parental strains were cultured separately in shake flasks in an aqueous medium having the following composition:

| Sucrose | 36 g/l |
|---|---|
| L-Asparagine | 7.5 g/l |
| $KH_2PO_4$ | 15 g/l |
| $K_2HPO_4$ | 21 g/l |
| $Na_2SO_4$ | 0.75 g/l |
| $Mg\ SO_4.7H_2O$ | 0.18 g/l |
| Salts solution | 1 ml/l |
| $CaCl_2$ | 0.06 g/l |
| Natural pH | |

The "salts solution" contained:

| $Fe\ (NH_4)_2\ (SO_4)_2.6H_2O$ | 15 g/100 ml |
|---|---|
| $Mn\ SO_4.4H_2O$ | 3 g/100 ml |
| $Zn\ SO_4.7H_2O$ | 3 g/100 ml |
| $Cu\ SO_4.5H_2O$ | 0.8 g/100 ml |

The medium was dispensed in 40 ml aliquots in 250 ml conical flasks. After autoclaving for 20 mins. at 121° C., 1 ml of sterile glucose solution (10.8% w/v) was added to each flask. The flasks were then supplemented with the appropriate amino acid auxotrophic requirements of the parent strains at a final concentration of 0.01%. In addition each flask was supplemented with 2 ml of sterile aqueous medium of the following composition:

| Sucrose | 25 g/l |
|---|---|
| Corn steep liquor | 0.1% as nitrogen |
| Ammonium acetate | 5.5 g/l |
| $CaCO_3$ | 5 g/l |

The pH was adjusted to 6.5 with KOH before autoclaving at 121° C. for 20 minutes.

Each shake flask was then inoculated with the appropriate strain, incubated for 48 hours for the white strain and 72 hours for the red strain (25° C., 250 rpm) and used to inoculate a second flask of the same medium (40 ml). This was harvested after 48 or 72 hours respectively and the mycelium was recovered by vacuum filtration through filter paper. After washing the mycelium two or three times with distilled water, the mycelium (total wet weight 1-2 g) was resuspended in 0.01 M dithiothreitol in pH 7.3. citrate/phosphate buffer (10 ml) and incubated at 30° C. for 1 hour with gentle shaking.

The dithiothreitol-treated mycelium was washed with distilled water and resuspended in pH 6.8 buffer (10 ml) containing Cytophaga enzyme $L_1$ (20 mg; available from BDH), and further containing 0.8 M NaCl and 0.02 M $MgSO_4$. The suspension was incubated at 30° C. for 3 hours with gentle shaking.

The resulting mixture of protoplasts and partially digested mycelium was filtered through cotton wool to remove the mycelium and the filtrate was centrifuged at 700 g for 5 mins. The pellet was washed twice with isotonic saline (0.9 M sodium chloride) and finally resuspended in isotonic saline.

The production of protoplasts was confirmed by the appearance of small spherical cells that were quite distinct from the undigested mycelium fragments. The viability of the protoplasts could be determined by plating out onto osmotically stabilised (2% sucrose and 0.8 M NaCl) and non-stabilised heart infusion agar (Bacto heart infusion broth (Difco) gelled with Oxoid agar).

The protoplasts were osmotically fragile and did not survive on non-stabilised agar. The viability of the protoplasts was about 70%, and about 15% of the growth on the stabilised agar was due to mycelial fragments.

Protoplasts from each parental strain ($1-2 \times 10^6$ of each auxotroph per ml) were suspended in isotonic saline (5 ml), mixed together and centrifuged at 700 g for 5 mins. The pellet was resuspended in a 30% solution of polyethylene glycol (mol. wt. 6000) in pH 7.5. glycine buffer (2 ml) containing 0.01 M calcium chloride, which had been prewarmed to 30° C., and incubated at 30° C. for 10 mins. After dilution with isotonic saline (6 ml) the preparation was centrifuged at 700 g for 5 mins, washed twice with isotonic saline and finally resuspended in isotonic saline.

The fusion mixture was initially plated out on the series of osmotically stabilised selective regeneration media listed in the column headings to the Table below. Spores and hyphal fragments were taken from the growth centres on the regeneration media and were plated onto minimal medium and complete medium. Repeated successive plating of the resulting colonies on minimal medium and complete medium resulted in purification of the progeny and provided a stability test.

The minimal medium (Czapek Dox minimal agar) had the composition by weight:

| (Czapek Dox) | |
|---|---|
| Sucrose | 3% |
| $NaNO_3$ | 0.2% |
| $KH_2PO_4$ | 0.1% |
| $MgSO_4.7H_2O$ | 0.05% |
| KCl | 0.05% |
| $FeSO_4$ | 0.001% |
| Agar (Oxoid No. 3) | 2% |

The pH was adjusted to 6.8 with KOH before autoclaving at 121° C. for 20 mins.

The complete medium (Sabourauds' Agar) had the composition by weight:

| Maltose | 4% |
|---|---|
| Peptone (Oxoid neutralised bact.) | 1% |
| Malt Extract (Oxoid) | 2.4% |
| Agar (Oxoid No. 3) | 2% |

The pH was adjusted to 7.5 with NaOH before autoclaving at 121° C. for 20 mins.

The resulting purified colonies from complete medium were than characterized, with regard to colour and growth requirements, as the strains listed in the Table below. The number of such strains recovered from each selective medium is recorded in the Table. Strains included prototrophs which did not segregate on treatment with p-fluorophenylalanine or gamma-rays. "MM" indicates minimal medium and "MM+" indicates osmotically stabilised minimal medium.

TABLE I

| | Selective Regeneration Medium | | | | |
|---|---|---|---|---|---|
| Strains | MM+ | MM+ + Arginine | MM+ + Methionine | MM+ Leucine + Leucine | MM+ + Methionine | Total |
| Red Arg Leu (Paren- | | | | | | |

TABLE I-continued

| Strains | MM+ | MM+ + Arginine | MM+ + Methionine | MM+ + Leucine | MM+ + Leucine + Methionine | Total |
|---|---|---|---|---|---|---|
| (Paren)tal) [Whi Arg Met Parental] | 1 | 1 | 1 | 8 | 7 | 18 |
| Red Leu Met (Parental) | | 11 | 8 | | 13 | 32 |
| Whi Leu Met | | | | 2 | | 2 |
| Red Arg Met | | | | 3 | | 3 |
| Whi Arg Leu | | | | 2 | | 2 |
| Red Arg Whi Leu | | | | 1 | 4 | 5 |
| Red Arg | 3 | 4 | 2 | 1 | | 10 |
| Whi Arg | 1 | 7 | 13 | 2 | 3 | 26 |
| Red Leu | | | | 5 | 3 | 8 |
| Whi Leu | | | | 3 | 11 | 14 |
| Red Met | 1 | | | | 1 | 2 |
| Whi Met | | 1 | 1 | 1 | 4 | 7 |
| Red | 3 | 1 | 1 | 1 | 2 | 8 |
| Whi | 18 | 6 | 12 | 8 | 15 | 59 |
| Red Arg Leu Met | | | | | | |
| Whi Arg Leu Met | | | | 1 | 1 | 2 |

The growth rates and sporulation characteristics of the progeny isolated were determined.

Table II shows a comparison of growth rates on solid medium and in submerged culture in the above medium of the parent strains and a prototrophic progency, strain P.

Table III shows a comparison of sporulation data for the parent strains and a Whi Arg Met progeny, strain Q.

Strain P showed a growth rate, both on solid medium and in submerged culture, significantly greater than that of either parent while strain Q showed a degree of sporulation also significantly greater than that of either parent.

TABLE II

| Characteristic | Parent Strain Red Arg Leu | Parent Strain Whi Arg Met | Prototrophic Progeny Strain P |
|---|---|---|---|
| Growth rate on solid medium (mm/hr on Sabouraud's agar) | 0.031 | 0.063 | 0.083 |
| Growth in submerged culture (g. dry weight/liter after 5 days) | 2.5 | 7.2 | 17.3 |

TABLE III

| Characteristic | Parent Strain Red Arg Leu | Parent Strain Whi Arg Met | Progeny Strain Q Whi Arg Met |
|---|---|---|---|
| Sporulation (average no. of spores per colony on Sabouraud's agar after 3 weeks at 25° C.) | <$10^3$ | <$10^3$ | $10^7$ |

EXAMPLE 2

Two highly divergent strains of *A. chrysogenum*, strains A and B, both derived from *A. chrysogenum* ATCC 14553, had the characteristics shown in Table IV.

Auxotrophic markers were introduced into both strains by conventional mutation techniques. Thus spores from each strain were subjected to far ultra-violet light such that about 99% of the spores were killed. The survivors were then tested for growth requirements and a mutant of each strain was selected which showed suitable growth-requirement mutations to act as auxotrophic markers. A mutant of strain A having an aneurine requirement in addition to the nicotinamide requirement shown in Table IV and a mutant of strain B having a requirement for both arginine and aneurine were thus selected.

According to the methods of Example 1, these two marked strains were then separately cultured for 48 hours, protoplasts were prepared from the mycelium of each strain and the protoplasts of the two strains were mixed and fused.

The fusion mixture was plated out onto osmotically stabilised minimal medium. Spores and hyphal fragments were taken from the growth centres and were then plated onto complete medium. The minimal and complete media had the compositions given in Example 1. The resulting colonies were characterised with regard to, for example, colour, growth and cephalosporin C production.

Of some 600 prototrophic or nicotinamide-requiring progeny, 35 were thus found to have cephalosporin C titres in excess of either parent, i.e. in excess of 100 units, when cultured under the same conditions.

One progeny, strain R, had the characteristics shown in Table IV. Strain R showed a cephalosporin C titre significantly greater than that of either parent, and had a growth rate and degree of sporulation intermediate between that of the two parents.

TABLE IV

| Characteristic | Parent Strains Strain A | Parent Strains Strain B | Progeny Strain R |
|---|---|---|---|
| Growth requirements | Nicotinamide | None | Nicotinamide |
| Mycelial colour | Red | White | White. |
| Ability to use sulphate in cephalosporin synthesis | Yes | No | Yes |
| Cephalosporin C production | 100 units | 30 units | 210 units |
| Growth rate (mm/hr) on Sabourauds' agar | 0.012 | 0.083 | 0.042 |
| Sporulation (average no. of spores per colony on Sabourauds' agar after 3 weeks at 25° C.) | <$10^3$ | $10^6$ | $10^5$ |

EXAMPLE 3

An auxotrophic mutant derived from *A. chrysogenum* strain M8650 (ATCC 14553) was crossed with an auxotrophic mutant derived from strain C0728 (IMI237183) which was itself derived from strain M8650 by several conventional mutation steps. The cross was Arg Met (M8650)×Leu (C0728). The abbreviations Arg, Met, Leu indicate a requirement for arginine, methionine or leucine respectively. The two auxotrophic parent strains have been deposited under accession numbers IMI227145 and IMI237183ii respectively.

According to the methods of Example 1, these two marked strains were separately cultured for 48 hours, protoplasts were prepared from the mycelium of each strain and the protoplasts of the two strains were mixed and fused.

The fusion mixture was plated out onto osmotically stabilized minimal medium. Spores and hyphal fragments were taken from the growth centres and were then plated onto minimal medium and complete medium to confirm the stability of the isolates. The minimal and complete media had the compositions given in Example 1.

The stable prototrophic recombinants obtained from this cross and the parent strains were separately fermented as follows. The strains were cultured on Sabouraud's Agar (recipe given in Example 1) for 10 days at 25° C. Scrapes of spores and hyphal fragments from these cultures were used to inoculate shake flasks containing medium (16 ml) of the following composition:

"Seed Stage" Medium

| Corn steep liquor | 0.1% as nitrogen |
|---|---|
| Ammonium acetate | 5.5 g/l |
| Sucrose | 25 g/l |
| Calcium carbonate | 10 g/l |

The pH was adjusted to 6.5 with NaOH. After autoclaving at 121° C. for 20 minutes the shake flasks were incubated for 48 hours (25° C., 250 rpm). An inoculum of 0.5 ml was then taken from each shake flask and used to inoculate a second shake flask containing medium (9.5 ml) of the following composition:

| Corn steep liquor | 0.5% nitrogen |
|---|---|
| Lactose | 46 g/l |
| Glucose | 2 g/l |
| Methionine | 2.3 g/l |
| Phenyl acetyl ethanbolamine | 1.5 g/l |
| Calcium carbonate | 16 g/l |
| Urea | 0.8 g/l |
| Ammonium sulphate | 3.4 g/l |
| Maize oil | 6 drops per flask |

The pH was adjusted to 6.6 with NaOH. After autoclaving at 121° C. for 20 minutes the shake flasks were incubated for 120 hours (25° C., 250 rpm).

The particular improved property observed in the recombinant strains which we isolated was an improved titre of desacetylcephalosporin C, which was assayed chemically. The results are shown in Table V.

TABLE V

| Strain | Chemical Assay (μg/ml) Desacetyl Cephalosporin |
|---|---|
| M8650 | 0 |
| C0728 | 310 |
| Recombinant 1 | 827 |
| Recombinant 2 | 809 |
| Recombinant 3 | 843 |

What is claimed is:

1. A method of producing an improved strain of *Acremonium chrysogenum* which comprises submitting parent strains of *Acremonium chrysogenum* to protoplast fusion and nuclear fusion and selecting and propagating said improved strain from the protoplast and nuclear fused progeny or from a mutant thereof.

2. A method as claimed in claim 1 wherein the parent strains are treated to facilitate the selection of the progeny.

3. A method as claimed in claim 2 wherein each of the parent strains is genetically marked with auxotrophic markers prior to protoplast fusion and nuclear fusion.

4. A method as claimed in claim 3 wherein each parent strain is genetically marked with at least two auxotrophic markers.

5. A method as claimed in claim 2 wherein each of the parent strains is genetically marked by colour or drug resistance prior to protoplast fusion and nuclear fusion.

6. A method as claimed in claim 1 wherein the parent strains are each treated with a different irreversible metabolic inhibitor prior to protoplast fusion and nuclear fusion to effect different and complementary metabolic inhibitory effects.

7. A method as claimed in claim 1 wherein the protoplast fusion is effected in the presence of a polyethylene glycol having a molecular weight in the range 1000–8000.

8. A method as claimed in claim 1 wherein the protoplast fusion is effected in the presence of calcium ions at a concentration of 0.002–1.0 M.

9. An improved strain of *Acremonium chrysogenum* produced by submitting parent strains of *Acremonium chrysogenum* to protoplast fusion and nuclear fusion and selecting and propagating said improved strain from the protoplast and nuclear fused progeny or from a mutant thereof.

10. A method of producing a cephalosporin which comprises culturing an improved strain of *Acremonium chrysogenum*, produced by protoplast fusion and nuclear fusion of parent strains of *Acremonium chrysogenum* and selecting and propagating said improved strain from the protoplast and nuclear fused progeny or a mutant thereof, and isolating the desired cephalosporin or a cephalosporin derivative thereof from the culture medium.

11. The improved strain of claim 9 wherein the progeny is a progeny having a significantly greater growth rate than either parent.

12. The improved strain of claim 9 wherein the progeny is a progeny having a significantly greater degree of sporulation as compared with either parent.

* * * * *